(12) United States Patent
Escobar Hernández et al.

(10) Patent No.: US 10,988,420 B2
(45) Date of Patent: Apr. 27, 2021

(54) NANOPARTICLES OF LAYERED DOUBLE HYDROXIDES CONTAINING NON-POLAR COMPOUNDS OF PLANT ORIGIN, AND METHOD FOR THE SEPARATION AND SELECTIVE RELEASE OF SAID COMPOUNDS

(71) Applicant: UNIVERSIDAD DE GUADALAJARA, Jalisco (MX)

(72) Inventors: Daniel Escobar Hernández, Jalisco (MX); Michel Jorgelina Montoya Gutiérrez, Sinaloa (MX); Gregorio Guadalupe Carbajal Arízaga, Jalisco (MX)

(73) Assignee: UNIVERSIDAD DE GUADALAJARA, Jalisco (MX)

( * ) Notice: Subject to any disclaimer, the term of this patent is extended or adjusted under 35 U.S.C. 154(b) by 0 days.

(21) Appl. No.: 16/062,717

(22) PCT Filed: Dec. 13, 2016

(86) PCT No.: PCT/IB2016/057578
§ 371 (c)(1),
(2) Date: Nov. 21, 2018

(87) PCT Pub. No.: WO2017/103787
PCT Pub. Date: Jun. 22, 2017

(65) Prior Publication Data
US 2019/0092710 A1   Mar. 28, 2019

(30) Foreign Application Priority Data

Dec. 15, 2015 (MX) .................. MX/a/2015/017358

(51) Int. Cl.
| | | |
|---|---|---|
| C07C 7/12 | (2006.01) |
| B01J 20/06 | (2006.01) |
| A61K 47/02 | (2006.01) |
| A61K 47/46 | (2006.01) |
| A61K 9/51 | (2006.01) |
| B01J 20/28 | (2006.01) |
| B01D 11/02 | (2006.01) |
| B01D 21/26 | (2006.01) |
| C07C 7/00 | (2006.01) |
| B82Y 30/00 | (2011.01) |
| B82Y 40/00 | (2011.01) |

(52) U.S. Cl.
CPC ............. *C07C 7/12* (2013.01); *A61K 9/5115* (2013.01); *A61K 9/5176* (2013.01); *A61K 9/5192* (2013.01); *A61K 47/02* (2013.01); *A61K 47/46* (2013.01); *B01D 11/0288* (2013.01); *B01D 21/262* (2013.01); *B01J 20/06* (2013.01); *B01J 20/28007* (2013.01); *C07C 7/005* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 2011/0060072 A1* | 3/2011 | Martin | ................... | B82Y 30/00 523/105 |
| 2012/0309651 A1* | 12/2012 | Pregibon | .............. | C12Q 1/6816 506/16 |
| 2013/0192835 A1* | 8/2013 | Vorderbruggen | ........ | E21B 43/04 166/305.1 |
| 2015/0047848 A1* | 2/2015 | Bestaoui-Spurr | ........ | E21B 43/04 166/305.1 |
| 2015/0104647 A1* | 4/2015 | Bestaoui-Spurr | ...... | C09K 8/805 428/404 |
| 2015/0166355 A1* | 6/2015 | O'Hare | ................... | C01F 7/005 524/429 |

FOREIGN PATENT DOCUMENTS

| | | |
|---|---|---|
| WO | 2007067043 A1 | 6/2007 |
| WO | 2012059936 A1 | 5/2012 |

OTHER PUBLICATIONS

Itaciara Larroza Nunes et al., "Encapsulation of lycopene using spray-drying and molecular inclusion processes", Braz. Arch. Biol. Technol., pp. 1-8, vol. 50 No. 5 Curitiba (Sep. 2007).
Hazuki Nerome et al., "Nanoparticle formation of lycopene/β-cyclodextrin inclusion complex using supercritical antisolvent precipitation", The Journal of Supercritical Fluids, pp. 97-103, vol. 83, (Nov. 2013).
Chiu Y. et al "Encapsulation of Lycopene extract from tomato pulp waste with gelatin and poly(gamma-glutamic acid) as carrier". Journal of Agricultural Food Chemistry, pp. 5123-5130, vol. 55(13) (Jun. 2007).
Tatiana Calvo, "Encapsulación de licopeno empleando polielectrolitos. Influencia del secado y congelado sobre su estabilidad", Biblioteca Digital de la Universidad de Buenos Aires, (Dec. 2013) English Abstract Attached.

(Continued)

*Primary Examiner* — Tam M Nguyen
(74) *Attorney, Agent, or Firm* — Browdy and Neimark, PLLC

(57) ABSTRACT

The present invention relates to layered double hydroxides (LDH) nanoparticles containing a non-polar compound of plant origin, which provide said non-polar compounds with higher stability and photodegradation resistance, in order to increase their shelf and storage life. Furthermore, it is described a simple and economical method for separating a non-polar compound from a plant material that contains it, as well as a method for selectively releasing the non-polar compound of plant origin contained in the LDH nanoparticles, with a high purity.

5 Claims, 2 Drawing Sheets

(56) References Cited

OTHER PUBLICATIONS

Martínez, David R. et al., "Hidróxidos dobles laminares: arcillas sintéticas con aplicaciones en nanotecnología", Avances en Química, 7(1), pp. 87-99 (May 2012).

Kohno, Y. et al.,"Improved photostability of hydrophobic natural dye incorporated in organo modified hydrotalcite", Journal of Physics and Chemistry of Solids 945-950, vol. 75(Mar. 2014).

Iyi, N. et al. Deintercalation of carbonate ions and anion exchange of an Al-rich MgAl-LDH (layered double hydoxide) Applied Clay Science pp. 246-251, vol. 42 (Feb. 2008).

\* cited by examiner

NANOPARTICLES OF LAYERED DOUBLE HYDROXIDES CONTAINING NON-POLAR COMPOUNDS OF PLANT ORIGIN, AND METHOD FOR THE SEPARATION AND SELECTIVE RELEASE OF SAID COMPOUNDS

FIELD OF INVENTION

The present invention is related to the techniques of separating compounds of plant origin from its plant source for their later application, and more particularly, it is related to the separation of non-polar compounds of plant origin by the synthesis of layered double hydroxides in situ in a plant material containing said non-polar compound, and a method for selectively releasing the separated compound.

BACKGROUND OF THE INVENTION

Chemical substances found in plants are of great interest in the technological field due to their beneficial properties for human beings in several applications, ranging from applications in the medicine field and the cosmetic, food and chemical industries, among others. An example of these types of compounds is carotenoids, which can be found in several plant sources such as fruits and vegetables or other green vegetables. Carotenoids are mainly known as being responsible for the coloring in some vegetable foods and by performing a role as anti-oxidants in the protection of an organism from free-radicals, which has caused an increasing research for these types of compounds especially in the pharmaceutical industry, in order to treat certain diseases.

Several separation and extraction techniques have been developed in order to obtain these substances from their plant source in the most pure possible way so as to make the most of their use, wherein the most commonly known and utilized involve organic solvents, ultrasound devices, enzymes, or supercritical fluid extraction. However, the stringent conditions to which the plant source is subjected to in order to achieve the extraction or separation of the compound of interest through these means compromise the stability and properties of said compound of interest, especially with carotenoids which can seriously be affected by the simple light contact, i.e., because they undergo photo-degradation. Likewise, the high temperatures and pressures involved in some known methods cause the loss of the compound or a low purity thereof, which has negative effects in the efficiency of the separation carried out.

On the other hand, encapsulating techniques to protect these compounds of plant origin have been developed, wherein one of the most currently common is the use of cyclodextrines. However, said cyclodextrines are difficult to obtain and purify, which makes the separation or extraction method a complex method. In addition to the use of cyclodextrins, some encapsulating techniques further involve the use of supercritical gases or fluids with the purpose of speeding the extraction. However, the required stringent conditions puts at risk the stability of the plant source compound (Itaciara Larroza Nunes; Adriana Zerlotti Mercadante "*Encapsulation of lycopene using spray-drying and molecular inclusion processes*", Braz. Arch. Biol. Technol. vol. 50 no. 5 Curitiba September 2007; Hazuki Nerome et al "*Nanoparticle formation of lycopene/β-cyclodextrin inclusion complex using supercritical antisolvent precipitation*", The Journal of Supercritical Fluids, Volume 83, November 2013, Pages 97-103).

Currently, other techniques to separate plant compounds via encapsulation include the use of gelatin and glutamic acid, as described by Chiu Y. et al "*Encapsulation of Lycopene extract from tomato pulp waste with gelatin and poly(gamma-glutamic acid) as carrier*". Journal of Agricultural Food Chemistry, 2007, Jun. 27; 55(13):5123-30, or by means of liposomes or polymers as described by Padma Venkitachalam Devarajan et. al., in patent document WO2012059936A1. However, it is likewise necessary to use supercritical fluids, even with a previous purification of the plant compound, which compromises the separation efficacy, and the costs increase due to the used conditions, fluids and polymerizations. Further, the thermal stability of the compound is compromised, since the compound of interest is encapsulated within an organic compound, being thereby encapsulated in a medium similar to the plant source from which it becomes, and remaining susceptible to thermal degradation.

An additional problem following the encapsulation of the compounds of plant origin is the release of the compound of interest from said capsule. Currently, organic solvents are used to release the compound from the capsule (Tatiana Calvo, "*Encapsulación de licopeno empleando polielectrolitos. Influencia del secado y congelado sobre su estabilidad*", Biblioteca Digital de la Universidad de Buenos Aires, Dec. 9, 2012). However, the use of organic solvents limits the subsequent applications of the compound, particularly in medical fields, or on the contrary, subsequent purifications or additional processes are required to remove the remaining organic solvent.

On the other hand, layered double hydroxides (LDH) have been synthesized in the last years, also referred to as synthetic clays, which are synthetic compounds having structures formed by positively-charged metal hydroxide laminates, which are stabilized by inter-laminar anions. These compounds have been exploited in order to obtain new materials in the nanometric scale encompassing a wide range of applications, and to prepare functionalization or hybridation products with organic molecules (Martinez, David R., Carbajal, Gregorio G. "*Hidróxidos dobles laminares: arcillas sintéticas con aplicaciones en nanotecnología*", Avances en Quimica, 7(1), 87-99 (2012)).

In view of the above, the main feature of the layered double hydroxides is their capacity of interspersing and interchanging anions for those anions already present within the structure (for example: $CO_3^{2-}$, $NO_3^-$). Anions that may be interspersed are diverse, such as oxo-anions, anionic complexes, organic anions, surfactants, monomers, polymers, amino acids, peptides, organic complexes, vitamins, enzymes, genetic material and drugs such as anti-cancer, antibiotics, anti-inflammatory, anticoagulants, anti-hypertensive, sun-blockers, all them with anionic features. In the case of organic molecules, those being polar and having —COOH, —SO$_4$H, —PO$_3$H$_2$ groups can be interspersed, since when carrying out the interspersing, they are converted into their respective anions: —COO—, —SO$_4$—, —PO$_3$=. This technique is known as ionic interchange. However, from the experimental point of view, it is very complex to make such replacement, or it is time consuming due to the required conditions to make the ionic interchange.

On the other hand, the use of the layered double hydroxides with organic molecules is disclosed in the state of the art, for example in application WO 2007/067043 A1, wherein a preparation conceived to treat the mineral deficiency disorder was made, involving the synthesis of layered double hydroxides via ionic interchange in the presence of an anti-oxidant, wherein carotenoids are mentioned as one option. However, although carotenoids are mentioned, this document does not show any experimental evidence using the non-polar plant compounds, and for this reason, such compounds stayed out of the scope of said document. In addition, the document describes that the interspersing method is ionic interchange, which necessarily involves an anion as already explained, and thus, it is not possible to intersperse non-polar compounds. Moreover, in said application WO2007067043A1 it is taught that the presence of the anti-oxidant is to prevent the undesired oxidation of bivalent to trivalent cations in the layered double hydroxides, i.e., it does not show the anti-oxidant interspersing in any way. Thus, the application WO2007067043A1 is limited to describe the use of anionic or polar compounds as anti-oxidant additives in the synthesis of layered double hydroxides, but it does not describe the encapsulation of non-polar neutral compounds.

Accordingly, it has been sought to overcome the drawbacks of the separation, release and production methods for the compounds of plant origin currently used, and to increase the stability of these compounds sensitive to environmental factors such as temperature, pressure, humidity, sun-light, microbial attack, oxidation, and others, by developing layered double hydroxides nanoparticles containing non-polar compounds of plant origin, a method for separating and selectively releasing said compounds which, besides of providing a significantly higher thermal stability and a protection to the non-polar compounds of plant origin from environmental factors, allows to provide simpler separation/extraction methods, significantly economical and which improve the properties of the non-polar compounds of plant origin for subsequent applications.

OBJECTS OF THE INVENTION

Taking into account the defects of the prior art, it is an object of the present invention to provide layered double hydroxides nanoparticles containing non-polar compounds of plant origin.

It is another object of the present invention to provide non-polar compounds of plant origin such that they have a higher stability and photodegradation resistance in order to increase shelf and storage life thereof.

Likewise, it is yet another object of the present invention to provide a simple and economical method for separating non-polar compounds of plant origin, which does not involve solvents or stringent conditions which can compromise the properties of said non-polar compound of plant origin and allowing its obtainment with a high purity grade.

Another object of the present invention is to provide a method for releasing said non-polar compounds of plant origin once separated, being simple and economical for its easy application and manipulation of the separated plant compound.

These and other objects are achieved through the layered double hydroxides nanoparticles containing the non-polar compounds of plant origin, and the methods of separating and selectively releasing said compounds according to present invention.

BRIEF SUMMARY OF THE INVENTION

The present invention comprises in a first aspect layered double hydroxides nanoparticles containing a non-polar compound of plant origin.

In another aspect of the invention, it is considered a method for separating a non-polar compound from a plant material that contains it, comprising: conditioning the plant material having the non-polar compound; adding a metal-salts solution to the conditioned product; adding an alkali containing hydroxyl groups, thus producing a precipitate; and drying the obtained precipitate comprising layered double hydroxides nanoparticles containing a non-polar compound of plant origin.

Yet another aspect of the invention is a method for selectively releasing the non-polar compound of plant origin contained in the layered double hydroxides nanoparticles, which comprises the step of washing the layered double hydroxides nanoparticles containing a non-polar compound of plant origin with an acid solution, thereby obtaining a liquid phase containing the released non-polar compound of plant origin.

BRIEF DESCRIPTION OF THE DRAWINGS

The novel aspects, considered characteristic of the present invention, will be particularly set forth in the appended claims. However, some embodiments, features and some objects and advantages thereof, will be better understood from the detailed description read together with the appended drawings, wherein:

DETAILED DESCRIPTION OF THE INVENTION

Figures 1A, 1B:
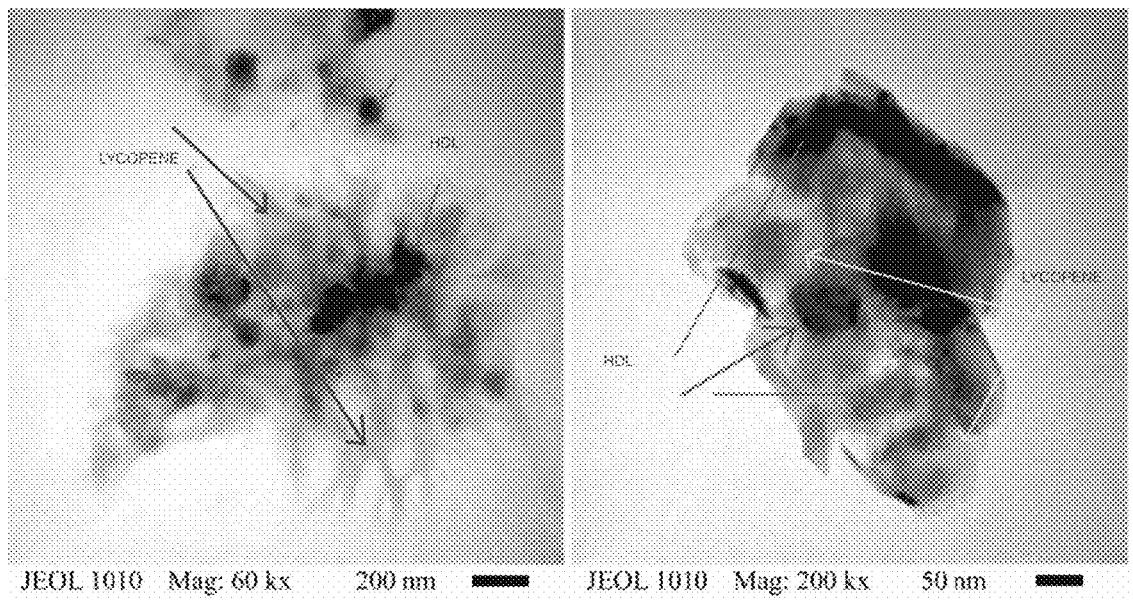
FIG. 1A shows a photomicrograph of 200 nm layered double hydroxides (LDH) nanoparticles with a non-polar compound of plant origin (lycopene) encapsulated inside according to a preferred embodiment of the present invention.
FIG. 1B shows a photomicrograph of 50 nm layered double hydroxides nanoparticles with a non-polar compound of plant origin (lycopene) encapsulated inside according to a preferred embodiment of the present invention.

It has been surprisingly found that synthesizing layered double hydroxides in situ in the plant material containing a non-polar plant compound, allows, in a single step, to obtain layered double hydroxides nanoparticles encapsulating the non-polar compound of plant origin, offering a higher protection, shelf and storage life, thereby significantly increasing its thermal stability and resistance to photodegradation. Likewise, it has been found that in order to release the non-polar compound of plant origin, it is only necessary to wash it with a slightly acid treatment.

What it is surprising in the present invention, is that the non-polar compounds of plant origin are strictly neutral molecules, since they do not ionize nor form anions, and nevertheless, it is possible to intersperse and retain them in the layered double hydroxides nanoparticles.

Thus, in one aspect of the present invention, layered double hydroxides (LDH) nanoparticles containing a non-polar compound of plant origin are described.

In a preferred embodiment of the present invention, the non-polar compound to LDH nanoparticles ratio is in the range from 20% to 70% (w/w) of the non-polar compound. More preferably the ratio is 50±3% (w/w) of the non-polar compound and 50±3% (w/w) of the LDH nanoparticles, i.e., each gram of LDH nanoparticles has a gram of the non-polar compound.

In another preferred embodiment of the present invention, the non-polar compound of plant origin is a carotenoid. More preferably, the carotenoid is lycopene.

In another preferred embodiment of the present invention, the plant material from which the non-polar compound of plant origin is extracted is selected from the group comprising tomato (red tomato), carrot, watermelon, pink grapefruit, apricot, guava and papaya. More preferably, the plant material is tomato (red tomato) or carrot.

One of the advantageous effects is that the non-polar compound of plant origin contained in the LDH nanoparticles exhibits a higher thermal stability of up to 400% its thermal stability independently from the LDH nanoparticles.

In another aspect of the present invention, it is described a method for separating a non-polar compound from a plant material that contains it, said method comprises the steps of:
- conditioning the plant material;
- adding a metal-salts solution to the conditioned product;
- adding an alkali containing hydroxyl groups, thereby producing a precipitate; and
- drying the obtained precipitate comprising the layered double hydroxides nanoparticles containing a non-polar compound of plant origin.

In an embodiment of the method for separating a non-polar compound of a plant material, the conditioning of the plant material comprises a grinding step to obtain a plant material juice.

In the metal-salts addition step, in a preferred embodiment of the present invention, said metal-salts are selected from nitrates, halogenides, and sulfates, wherein the metal-salts solution comprises a mixture of at least two metal-salts, and wherein the ratio of one salt is greater than the ratio of the other salt. In a preferred embodiment, said metal-salts are selected from nitrates. In a yet further preferred embodiment, said nitrates are selected from magnesium or zinc and aluminum or iron or a combination thereof.

With respect to the alkali addition step, in an embodiment of the present invention the alkali is selected from the group consisting of Arrhenius bases, i.e. providing the media with OH ions, with NaOH, $NH_4OH$ and KOH being particularly preferred. In a preferred embodiment, the alkali is selected from sodium hydroxide (NaOH). Furthermore, the pH is adjusted to a slightly alkaline pH from about 7 and about 10 with the alkali addition.

In another preferred embodiment of the present invention, the alkali addition step is carried out gradually.

In a preferred embodiment of the method for separating a non-polar compound from a plant material that contains it, the alkali addition is carried out at normal room temperature and atmospheric pressure.

In a preferred embodiment of the separation method, the temperature in the drying step is in the range from about 50° C. to about 100° C. during a period of time in the range from 15 to 36 hours.

In an optional embodiment of the method for separating a non-polar compound from a plant material that contains it, before carrying out the drying, in order to assure the compacting of the solid obtained, the method further comprises a centrifugation step at a speed of between 500 and 5000 rpm.

A main advantage of the separation method of the present invention over the extraction methods known in prior art is that the separation occurs by encapsulating the non-polar compound of plant origin in the layered double hydroxides nanoparticles being synthesized in situ in the plant material. This encapsulation occurs in a single step at the time of adding the alkali.

The simplicity of this method provides significant advantages in the economical aspect since it does not require any aggressive solvent, or any other organic or complex component in order to be able to separate the non-polar compound of interest from the plant material.

In still another aspect of the invention, a method for selectively releasing the non-polar compound of plant origin contained in the layered double hydroxides nanoparticles is provided, in a simple and economical manner, for its subsequent application or use.

The selective release method is advantageous since it does not use organic solvents, which cause additional steps in order to purify the released compound, and it releases the non-polar compound with a high purity for its subsequent use.

The method for selectively releasing a non-polar compound of plant origin contained in the layered double hydroxides nanoparticles, comprises the step of washing the layered double hydroxides nanoparticles containing a non-polar compound of plant origin with an acid solution.

In a preferred embodiment of the selective release method, the washing is carried out stirring, with a Brønsted acid solution, i.e. substances capable of donning a proton (H+) to the medium. Optionally, the washing can be carried out at normal environmental temperature and pressure conditions.

The present invention will be better understood from the following examples, which are given only for illustrative purposes in order to allow a better understanding of the preferred embodiments of the invention, without implying that there are no other non-illustrated embodiments which can be taken into practice based on the above detailed description.

EXAMPLES

A preferred embodiment of the present invention is illustrated by means of the following examples, in order to show the manner to carry out the same.

Example 1

An assay to separate and encapsulate lycopene was made (a non-polar compound) by means of LDH nanoparticles.

To this end, one saladette tomato (*Solanum lycopersicum* L.) was ground in a blender and the juice was filtered in a medium-pore paper filter (8 μm). 25 mL of this juice was taken and mixed with $0.30 \times 10^{-4}$ mol $Zn(NO_3)_2$ and $2.4 \times 10^{-5}$ mol $Al(NO_3)_3$. The mixture was stirred with a glass rod. Then 0.1 M NaOH was added until a pH=8 was reached. The mixture was stirred with a glass rod. All this was performed at room temperature. A red solid was immediately formed and sedimented.

In order to assure the compaction of the solid and to facilitate the washing, the suspension was centrifuged at 1,000 rpm during 4 minutes. The liquid phase was separated and the solid was washed with 50 mL distilled water. The solid was dried at 70° C. during 24 hours.

Figure 3:
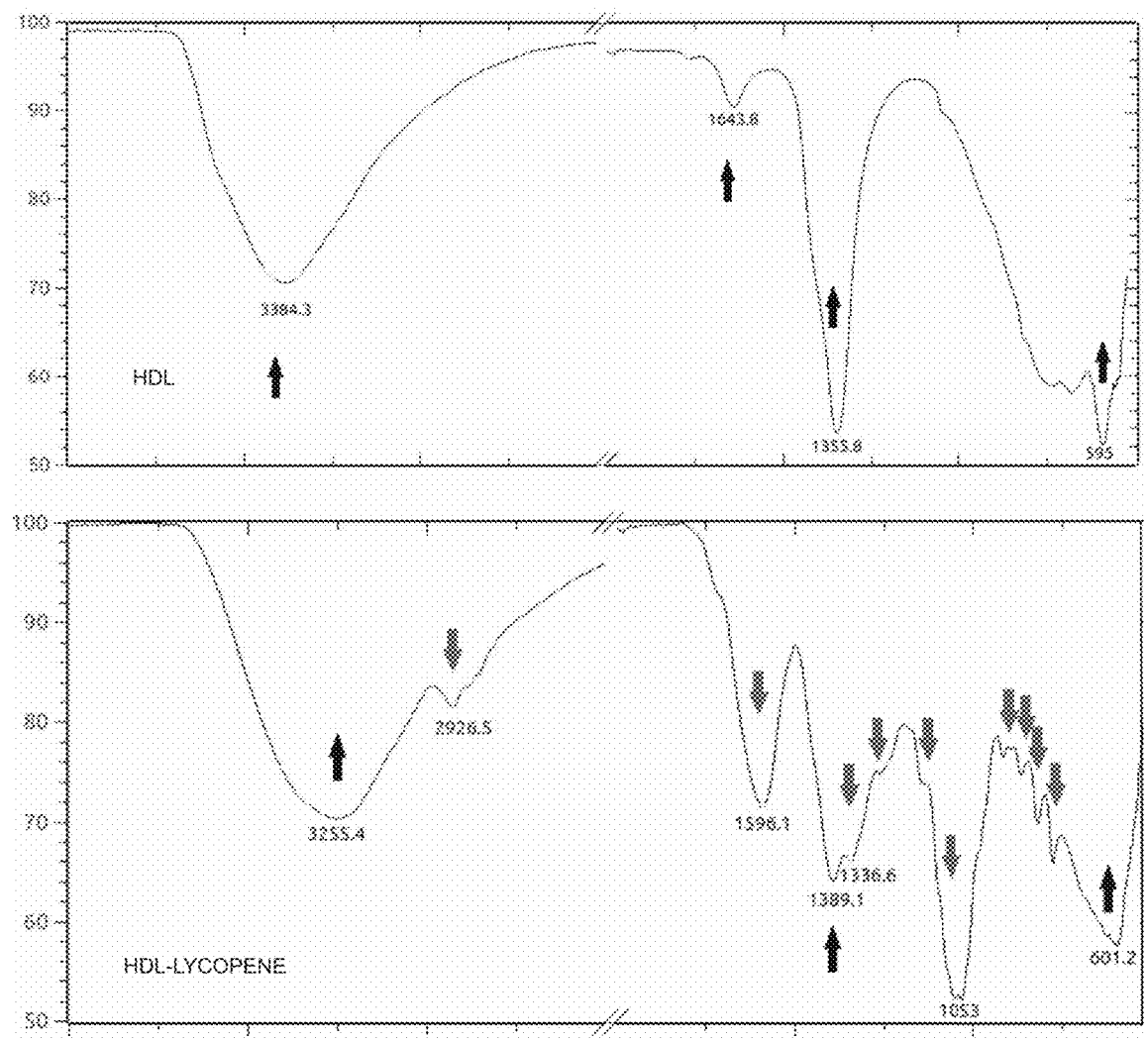
FIG. 3 shows a comparative infrared spectrum (IR) of reference LDH nanoparticles of the prior art and the IR spectrum of LDH nanoparticles with the non-polar plant compound.

The product which is obtained is a red powder. The presence of lycopene as the main component extracted from the tomato juice is evidenced by the IR spectrum shown in FIG. 3, wherein the typical IR spectrum of the layered double hydroxides nanoparticles and an IR spectrum of a LDH nanoparticles composition containing lycopene are compared.

The black arrows indicate the corresponding signals from the LDH nanoparticles and the red arrows the signals corresponding to lycopene. The purity of the lycopene as obtained was 93%, and the obtained nanoparticles are shown in FIGS. 1A and 1B illustrating photomicrographs obtained by transmission electronic microscopy of the LDH nanoparticles containing lycopene, in which the arrows indicate the location of each component, collected with amplifications of 60,000-fold (60 kX) and 200,000-fold (200 kx). It can be seen that the darker points are the LDH and the lighter points correspond to the encapsulated lycopene. The transmission electronic microscopy helps to detect that the LDH particles have nanometric dimensions.

Example 2

Another assay was performed using the same methodology than in example 1, except for the single variation in the amount of the metal-salts used, wherein in this example $2.06 \times 10^{-4}$ mol $Zn(NO_3)_2$ and $3.5 \times 10^{-5}$ mol $Al(NO_3)_3$ were used. The concentration ratio of the LDH nanoparticles and the obtained lycopene was of 0.5:1.5 molar ratio. The purity of the obtained lycopene was 92%.

Example 3

Another assay was performed using the same methodology than in example 1, except for using a concentration of $1.34 \times 10^{-4}$ mol $Zn(NO_3)_2$ and $4.4 \times 10^{-5}$ mol $Al(NO_3)_3$, wherein it was determined that the concentration of LDH nanoparticles with respect to lycopene was 1:1. The purity of the obtained lycopene was 95%.

Example 4

Another assay was performed using the same methodology than in example 1, except for using a concentration of $1.34 \times 10^{-4}$ mol $Mg(NO_3)_2$ and $4.4 \times 10^{-5}$ mol $Al(NO_3)_3$, wherein it was determined that the concentration of LDH nanoparticles with respect to lycopene was 1:1.5. The purity of the obtained lycopene was 94%.

Example 5

Figure 2:
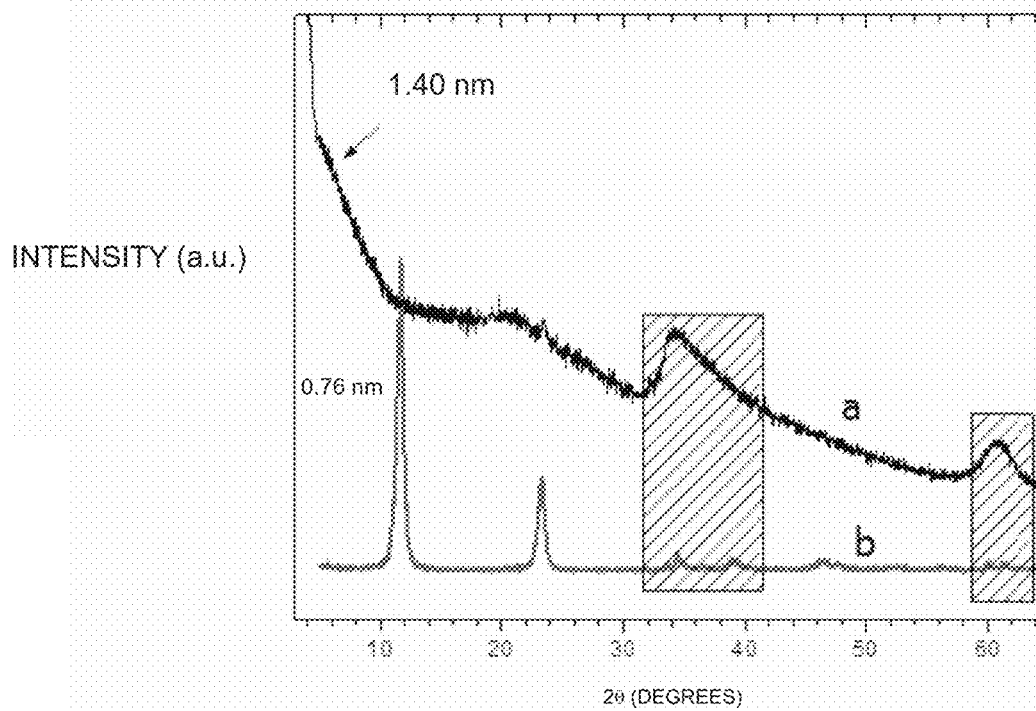
FIG. 2 shows a comparative plot of the X-ray diffraction pattern of reference LDH nanoparticles (a) of LDH particles with the non-polar compound of plant origin (b).

The precipitate obtained in example 3 was characterized to show the presence of encapsulated lycopene in the layered double hydroxides nanoparticles. The presence of the layered double hydroxides nanoparticles was detected by X-ray diffraction as shown in FIG. 2. X-ray diffraction is the absolute technique which indicates the formation of the layered double hydroxides. In the diffraction profile shown in said FIG. 2, both a reference LDH (line b) and the LDH-lycopene product (line a) are shown. Signals in region from 5 to 12 degrees (2 theta) appear when the LDH are being formed. In addition, the signal marked as 1.40 nm suggests that, besides the lycopene surrounding the LDH nanoparticles, it is also interspersed within the nanoparticles, since said signal corresponds to the distance between laminates indicating that the lycopene is therebetween. If there were no lycopene, said distance should be near 0.76 nm (line b). The purity of the obtained lycopene was 95%.

Example 6

A thermogravimetric analysis (TGA) was performed to the product as obtained in examples 1-4 in order to evaluate the thermal stability and protection of the non-polar plant compound separated, by means of a thermal decomposition profile of the lycopene encapsulated in the LDH nanoparticles. The decomposition range for the LDH nanoparticles having lycopene (LDH-lycopene) starts at 375° C. and ends at 500° C. By heating the LDH nanoparticles-lycopene, a degradation of the nanoparticles occurs at 200-250° C., at which point water is released and this protects the lycopene, up to a temperature of 400° C.

With the above, we may conclude that thanks to the present invention, the thermal stability of the lycopene is surprisingly increased up to 400%, since in the prior art it is informed that the lycopene is decomposed at 100-150° C. (Antonio J. Meléndez-Martinez. *"Estabilidad de los pigmentos carotenoides en los alimentos"*. Area de Nutrición y Bromatología. Facultad de Farmacia. Universidad de Sevilla-Sevilla, España. Year 2004, Volume 54-Number 2) while with the present invention, the lycopene is degraded at temperature of 400° C.

According to the above-described, it may be seen that the layered double hydroxides nanoparticles containing non-polar compounds of plant origin, the methods of separating and selectively releasing said compounds, have been conceived to provide a higher thermal stability and protection of said compounds coming from a plant source, in order to increase their shelf and storage life, and it will be apparent to any skilled in the art that the embodiments of the layered double hydroxides nanoparticles containing non-polar compounds of plant origin, and methods of separating and selectively releasing said compounds as described above and illustrated in the accompanying drawings, are only illustrative and not limitative of the present invention, since many considerable changes are possible in its details without departing from the scope of the invention.

Therefore, the present invention should not be considered restricted except for the prior art demands and by the scope of the appended claims.

The invention claimed is:

1. Layered double hydroxides (LDH) nanoparticles, comprising a nonpolar compound of plant origin, wherein the percentage of the nonpolar compound in the LDH nanoparticles is in a range from 20% to 70% (w/w), and wherein the non-polar compound is a carotenoid.

2. The LDH nanoparticles according to claim 1, wherein the percentage of the nonpolar compound in the LDH nanoparticles is 50±3% (w/w).

3. The LDH nanoparticles according to claim 1, wherein the carotenoid is lycopene.

4. The LDH nanoparticles according to claim 1, wherein the plant material from which the carotenoid is extracted is selected from the group comprising tomato (red tomato), carrot, watermelon, pink grapefruit, apricot, guava and *papaya*.

5. The LDH nanoparticles according to claim 4, wherein the plant material from which the carotenoid is extracted is selected from tomato (red tomato) or carrot.

* * * * *